United States Patent [19]

Rollo et al.

[11] 4,113,614
[45] Sep. 12, 1978

[54] AUTOMATED HEMODIALYSIS TREATMENT SYSTEMS

[75] Inventors: Anita Hand Rollo, Hollywood; David Burrell Stearns, Lighthouse Point, both of Fla.

[73] Assignee: International Business Machines Corporation, Armonk, N.Y.

[21] Appl. No.: 749,585

[22] Filed: Dec. 10, 1976

[51] Int. Cl.² .................... B01D 13/00; B01D 31/00
[52] U.S. Cl. .................................. 210/22 A; 210/87; 210/90; 210/321 B
[58] Field of Search .................. 210/321 B, 22, 23 F, 210/85, 87, 90, 96 M, 137, 188; 137/99; 417/391, 393, 394, 395, 410, 419

[56] References Cited

U.S. PATENT DOCUMENTS

| 3,441,136 | 4/1969 | Serfass et al. | 210/321 B |
| 3,733,965 | 5/1973 | Braun | 91/275 |
| 3,795,318 | 3/1974 | Crane et al. | 210/321 B |
| 3,939,069 | 2/1976 | Granger et al. | 210/90 |
| 3,946,731 | 3/1976 | Lichtenstein | 210/87 |
| 4,021,341 | 5/1977 | Cosentino et al. | 219/321 B |

Primary Examiner—Charles N. Hart
Assistant Examiner—David R. Sadowski
Attorney, Agent, or Firm—John G. Wynn; Kenneth W. Hairston; J. Jancin, Jr.

[57] ABSTRACT

Disclosed herein are four embodiments of a system specifically applicable to the hemodialysis procedure. Two embodiments, configured as single pass and recirculating dialysate systems, control ultrafiltration rate to a preset value and measure ultrafiltration rate and the total quantity of ultrafiltrate removed. These embodiments are useful when the filtration characteristics of the dialyzer, i.e., semipermeable membrane, are constant and known. However, when the filtration characteristics of the dialyzer, i.e., semipermeable membrane, are not constant and known, two other embodiments, configured as single pass and recirculating dialysate systems, control transmembrane pressure to a preset value and measure ultrafiltration rate and total quantity of ultrafiltrate removed. All embodiments are closed systems requiring sealed dialyzers. Each of the foregoing systems include, inter alia, a unique flow measurement pressure control unit which controls fluid pressure and simultaneously meters fluid flow therein.

19 Claims, 7 Drawing Figures

AUTOMATED HEMODIALYSIS TREATMENT SYSTEMS

BACKGROUND OF THE INVENTION

1. Field of the Invention

The invention relates generally to the measurement of fluid flow and/or the control of fluid pressure in opened or closed fluid systems, and, in particular, to the measurement and control in closed systems of ultrafiltration in the hemodialysis procedure used in the treatment of kidney dysfunction and flood poisoning.

2. Description of the Prior Art

The normal kidney performs five basic functions, which are as follows: (1) removing the waste products of metabolism, (2) maintaining electrolyte equilibrium, (3) regulating water, (4) assisting in the regulation of blood pressure, and (5) assisting in the production of red blood cells.

The hemodialysis procedure is capable of accomplishing the first three functions only. Accordingly, removing waste and excess electrolytes are effected through diffusional mass transfer which is a function of the characteristics of the semipermeable membrane used and the concentration gradient across the semipermeable membrane. In addition, water is removed by imposing a pressure difference (transmembrane pressure) across the semipermeable membrane. This water, which is forced out of the blood into the dialysate, is called ultrafiltrate.

In most cases today, control of ultrafiltration is attempted through manual adjustment of blood flow rate and pressures, usually the pressure of the blood at the venuous return and/or the dialysate effluent pressure. The quantity of fluid actually removed is determined by weighing the patient before and after the hemodialysis treatment, computing the difference, and then correcting the difference for any extraneous causes for weight change, such as food or fluid intake. Control of ultrafiltration is based solely on the operator's experience in carrying out the above procedures. During the course of treatment, there is no dynamic means for determining actual ultrafiltration effected for the manual settings of pressure and flow. This is the more common technique used in hemodialysis treatment. Hence, there is a present need to provide improved method and apparatus for measuring and controlling ultrafiltration without effecting a new hemodialysis procedure.

Notwithstanding commonly used techniques, the ability to control ultrafiltration with a higher degree of certainty is much desired by the hemodialysis community. Consequently, researchers and hemodialysis equipment manufacturers have been working to provide solutions. Thus, some systems in current use provide the capability of measuring cumulative ultrafiltration. One such system features a regenerative dialysate supply means in which the dialysate volume is limited to the initial dialysate charge. Ultrafiltration increases the volume of the dialysate in the system and this change can be visually determined by means of a fluid level gage. However, all control is effected manually by conventional means, i.e., separate manual control of blood return pressure, blood flow rate and/or manual control of dialysate pressure. Generally, regenerative dialysate supply systems utilize an initial dialysate charge, for example six liters or less and have filter means in a fluid line to remove contaminants.

Another well known system uses a closed loop recirculating method which uses a fixed dialysate volume, for example, of 75 liters. The excess volume attributable to ultrafiltration is collected and measured in a graduated cylinder or its equivalent. Control of ultrafiltration is conventional for this negative pressure system which depends on blood pressure remaining constant for transmembrane pressure control. The suction pressure of the dialysate effluent (waste flow) is manually adjusted.

Notwithstanding a means for monitoring in one of the foregoing systems and a means for controlling transmembrane pressure in the other, there is a need for automated control of transmembrane pressure or ultrafiltration rate concurrently with metering and monitoring the ultrafiltration rate and the total quantity of ultrafiltrate removed.

The prior art, as indicated hereinabove, includes some advances in systems used for hemodialysis treatment. However, insofar as can be determined, no prior art system incorporates all of the features and advantages of the instant invention.

OBECTS OF THE INVENTION

Accordingly, a principal object of the present invention is to improve hemodialysis treatment without effecting a new hemodialysis procedure.

A further object of the present invention is to automate control of transmembrane pressure or ultrafiltration rate concurrently with metering and monitoring the ultrafiltration rate and the total quantity of ultrafiltrate removed.

Still a further object of the present invention is to tune-in a particular ultrafiltration rate, thereby maintaining a constant average transmembrane pressure.

Yet another object of the present invention is to tune-in a particular transmembrane pressure, thereby maintaining a near constant ultrafiltration rate.

SUMMARY OF THE INVENTION

In accordance with these and other objects and features of the present invention, four embodiments of an automated hemodialysis treatment system are disclosed. These are closed systems requiring sealed dialyzers. Two of the four embodiments are applicable when the filtration characteristics of the dialyzer are constant and known. The other two embodiments are applicable when the filtration characteristics of the dialyzer are not constant and known.

Briefly, the two principal embodiments (filtration characteristics of dialyzer constant and known) control ultrafiltration rate to a preset value and measure ultrafiltration rate and the total quantity of ultrafiltrate removed. Blood, from a patient under treatment, via a blood supply line is transported to a sealed dialyzer. The pressure of the blood in the blood supply line is sensed by a blood supply pressure sensing device. Blood leaving the sealed dialyzer is returned to the patient via a blood return line. Blood pressure at the blood return line is sensed by a blood return pressure sensing device. Dialysate, via a dialysate pump supply line is pumped by a dialysate supply constant volume displacement pump, via a dialysate supply line, to the sealed dialyzer. The blood side and the dialysate side of the sealed dialyzer are separated by a semipermeable membrane. The pressure of the dialystate at the dialystate supply line is sensed by a dialysate supply pressure sensing device. Dialysate effluent exits the sealed dialyzer, via a dialyzer effluent line, and is separated into two parallel paths. Through one path, the dialysate effluent is pumped, via a dialyzer effluent pump inlet line, by a dialyzer effluent constant volume displacement pump to an effluent receptacle. Dialysate effluent in the other path, via flow measurement pressure control unit input line flows to a flow measurement pressure control unit where it is used in the operation thereof after which via a flow measurement pressure control unit output line the dialysate effluent is routed to the effluent receptacle. Blood supply return and dialysate supply pressure sensing devices, aforementioned, convert the fluid pressures sensed into electrical signals which, in turn, via a dialysate supply pressure instrumentation conductor, a blood supply pressure instrumentation conductor and a blood return pressure instrumentation conductor, respectively, input to an ultrafiltration rate control unit. In addition, the ultrafiltration control unit is interfaced with the flow measurement pressure control unit via a sensor control instrumentation conductor. The characteristics of dialysate supply constant volume displacement pump and dialyzer effluent constant volume displacement pump are such that the volume of fluid pumped by each is equal. The flow measurement pressure control unit operates by using the fluid pressure in the system in cooperation with a motor-brake assembly which, in turn, cooperates with position sensing devices to generate electrical signals which are related to the volume of fluid leaving the flow measurement pressure control unit. A braking action, caused by a control signal generated by the ultrafiltration control unit, retards the motor-brake assembly, thereby modulating the pressure in the system. Alternately, the control signal generated by the ultrafiltration control unit can cause a pumping action which accelerates the motor-brake assembly, thereby modulating pressure in the system.

The flow measurement pressure control unit is applicable for the measurement of fluid flow (volume) and/or the control of fluid pressure in many types of open or closed fluid systems. It concurrently meters fluid flow and controls fluid pressure and interfaces with the ultrafiltration rate control unit aforementioned.

BRIEF DESCRIPTION OF THE DRAWINGS

The foregoing, other objects, novel features and advantages of the invention will be more apparent from the following, more particular description of the preferred embodiments as illustrated in the accompanying drawings, in which.

DESCRIPTION OF THE PREFERRED EMBODIMENTS

Figure 1A:
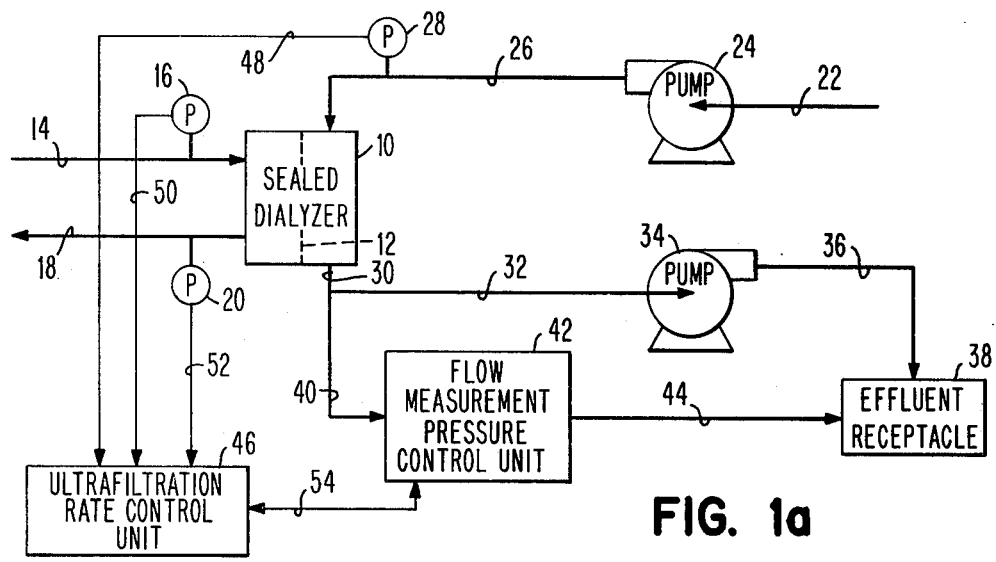
FIG. 1a depicts pictorially and in block diagram form a control ultrafiltration rate-single pass dialysate system in accordance with a principal embodiment of the present invention.
Figure 1B:
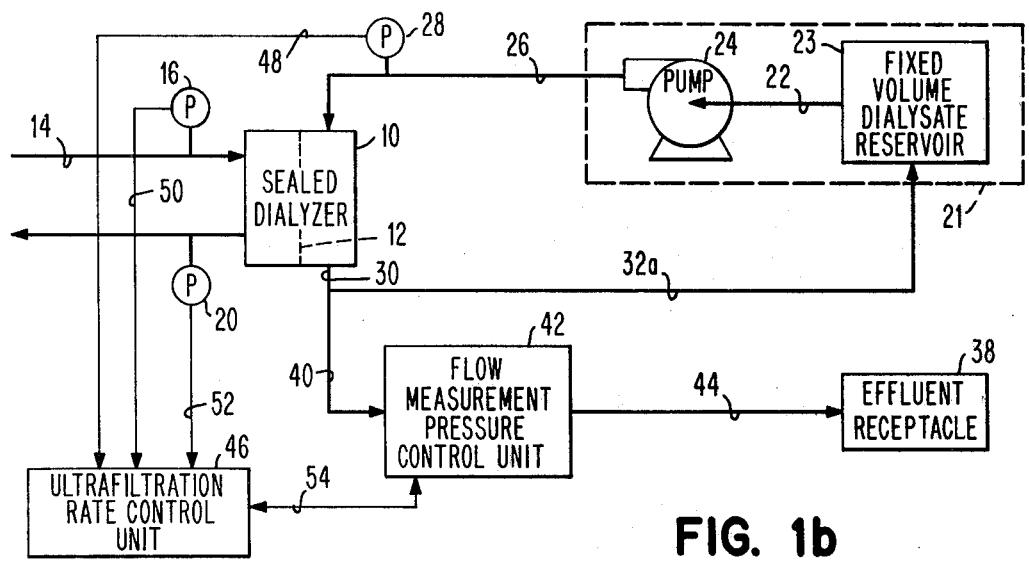
FIG. 1b depicts pictorially and in block diagram form a control ultrafiltration rate-recirculating dialysate system in accordance with another principal embodiment of the present invention.

The hemodialysis treatment systems of FIGS. 1a and 1b control ultrafiltration rate to a preset value and also measure ultrafiltration rate and the total quantity of ultrafiltrate removed. As aforementioned, these are closed systems and require a sealed dialyzer 10 having a semipermeable membrane 12 separating the blood side and the dialysate side thereof. The dialysate of FIGS. 1a and 1b are single pass dialysate systems operating at positive pressures and are directly applicable to capillary and plate type dialyzers. The filtration characteristics of semipermeable membrane 12, in sealed dialyzer 10, are constant and known.

Now referring to FIG. 1a, blood, from a patient under treatment, is transported to the blood side of sealed dialyzer 10 via blood supply line 14. The pressure of the blood is sensed at blood supply line 14 by blood supply pressure sensing device 16. Treated blood, leaving sealed dialyzer 10, is returned to the patient under treatment via blood return line 18. Blood return pressure sensing device 20 attached thereto senses the pressure.

Still referring to FIG. 1a, fresh dialysate via dialysate pump supply 22 is pumped by dialysate supply constant volume displacement pump 24 to dialysate supply line 26 which is connected to the dialysate side of sealed dialyzer 10. A dialysate supply pressure sensing device 28 is connected to dialysate supply line 26 to sense the pressure thereof. Continuing, dialysate effluent leaves sealed dialyzer 10 via dialyzer effluent line 30, the dialysate effluent therein dividing into two parallel pairs. One path, through dialyzer effluent pump inlet line 32, is connected to dialyzer effluent constant volume displacement pump 34 which, in turn, pumps the dialysate effluent, via dialyzer effluent pump outlet line 36, into effluent receptacle 38. The other path, through flow measurement pressure control unit input line 40 is connected to flow measurement pressure control unit 42. The dialysate effluent therefrom, via flow measurement pressure control unit output line 44, is routed to effluent receptacle 38 aforementioned.

Still referring to the single pass dialysate system of FIG. 1a, the pressures sensed by blood supply pressure sensing device 16, blood return pressure sensing device 20 and dialysate supply pressure sensing device 28 are converted, thereby, to electrical signals, proportional to the pressures sensed, which drive ultrafiltration rate control unit 46 via dialysate supply pressure instrumentation conductor 48, blood supply pressure instrumentation conductor 50 and blood return pressure instrumentation conductor 52, respectively. Finally, flow measurement pressure control unit 42 and ultrafiltration rate control unit 46 are interfaced by sensor-control instrumentation conductor 54 completing the system.

FIG. 1b is an alternate configuration for circulation of dialysate and control of ultrafiltration rate. The embodiment of FIG. 1b represents a recirculating system and is the preferred configuration for a fixed volume dialysate supply system. The basic difference between the embodiment of FIG. 1b and the embodiment of FIG. 1a, aforementioned, is that dialysate is applied to the system of FIG. 1b by dialysate circulator 21. Also, the dialyzer effluent from sealed dialyzer 10 at dialyzer effluent line 30 is routed to dialyzer circulator 21 via dialyzer effluent return line 32a. In this embodiment, dialyzer circulator 21 comprises a fixed volume dialysate reservoir 23 connected via dialysate pump supply line 22 to dialysate recirculating pump 24a. Operation with respect to ultrafiltration control is identical for the embodiments of FIGS. 1a and 1b and will hereinafter be explained in the "Statement of the Operation."

Figure 2A:
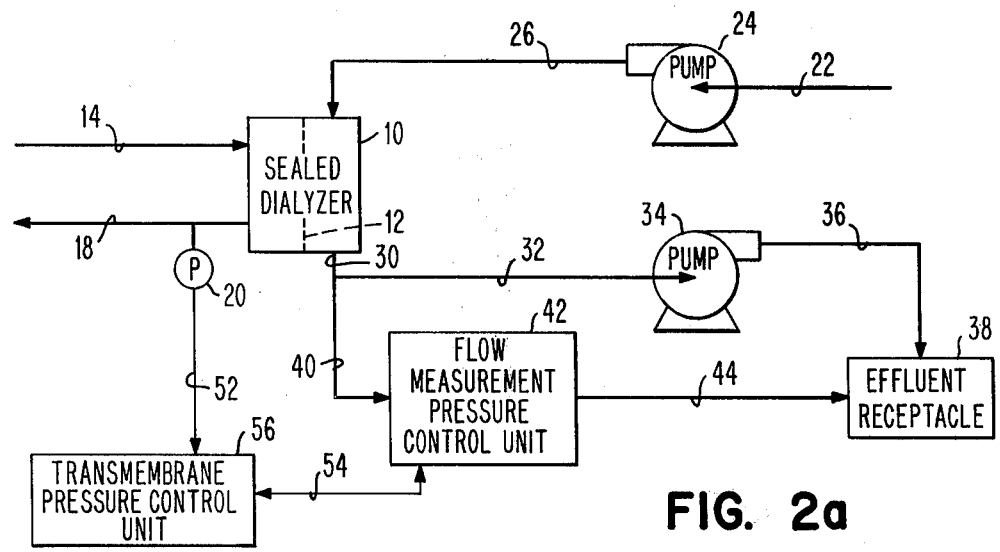
FIG. 2a depicts pictorially and in block diagram form a control transmembrane pressure-single pass dialysate system in accordance with yet another embodiment of the present invention.
Figure 2B:
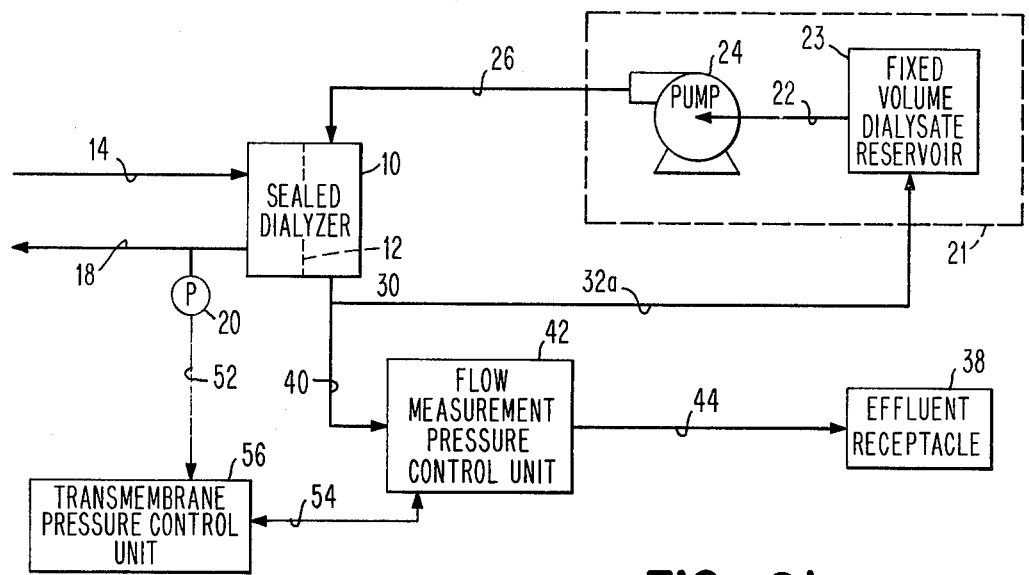
FIG. 2b depicts pictorially and in block diagram form a control transmembrane pressure-recirculating dialysate system in accordance with still another embodiment of the present invention.

Referring now to FIGS. 2a and 2b concurrently, in those cases where the filtration characteristics of dialyzer 10, and, accordingly, semipermeable membrane 12 are not constant and/or not known it is desirable to control transmembrane pressure to a preset value, measure ultrafiltration rate, and measure the total quantity of ultrafiltrate removed. The embodiments of FIGS. 2a and 2b accomplish these goals. These are also closed systems and require a sealed dialyzer 10. The elements in the FIGS. 2a and 2b are identical to the elements previously mentioned in the description of FIGS. 1a and 1b except that blood supply pressure sensing device 16 and its associated blood supply pressure instrumentation conductor 50 and dialysate supply pressure sensing device 28 and its associated dialysate supply pressure instrumentation conductor 48 are not required. Finally, ultrafiltration rate control unit 46 is replaced by transmembrane pressure control unit 56. (The inlet pressures of these two embodiments could be sensed as in FIGS. 1a and 1b for control of average transmembrane pressure rather than control of outlet transmembrane pressure. The control of only outlet transmembrane pressure yields substantially constant ultrafiltration). Hence, FIG. 2a is the control transmembrane pressure-single pass dialysate system embodiment and is the counterpart of the control ultrafiltration rate-single pass dialysate system of FIG. 1a. Also, the control transmembrane pressure-recirculating dialysate system of FIG. 2b is the counterpart of the control ultrafiltration rate-recirculating dialysate system of FIG. 1b. (The four configurations as described above, are shown with co-current flow of blood and dialysate. Alternately, these flows can be countercurrent or crosscurrent). Transmembrane pressure control unit 56 will be discussed more fully in the "Statement of the Operation" herein to follow.

Figure 3:
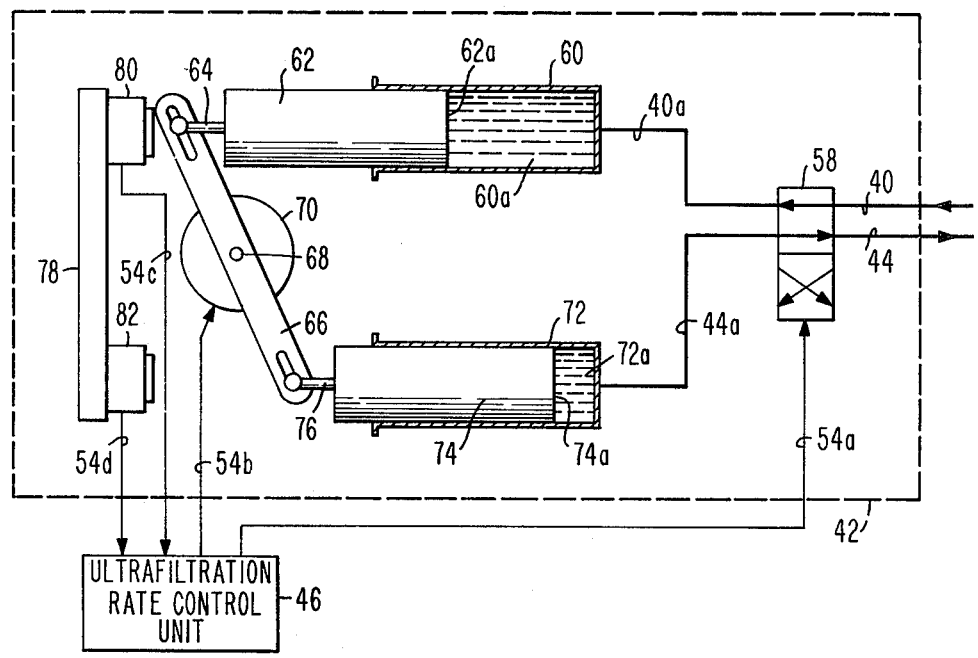
FIG. 3 depicts pictorially, schematically and in block diagram form the interfacing of the flow measurement pressure control unit and the ultrafiltration rate control unit as they relate to the embodiments of FIGS. 1a and 1b.

Referring now to FIG. 3, flow measurement pressure control unit 42, an indispensable element, used in all of the embodiments previously discussed, is shown in detail. Dialysate effluent enters and exits flow measurement pressure control unit 42 via flow measurement pressure control unit input line 40 and flow measurement pressure control unit output line 44, respectively. The dialysate effluent enters the system via four-way value assembly 58 and flows through input line 40a to fluid chamber 60 which fills with dialysate effluent 60a. Operatively connected to fluid chamber 60 is piston 62 having a front surface 62a. Connecting rod 64 being attached to piston 62 operatively connects piston 62 to one end of reciprocating motor lever arm 66. The center of the aforementioned lever arm is operatively connected by means of reciprocating motor shaft 68 to torque reciprocating motor 70. In this embodiment, the motor 70 has characteristics such that torque is proportional to current (amperes). Another fluid chamber 72, filled with dialysate effluent 72a which exits from flow measurements pressure control unit 42 via output line 44a, is operatively connected to piston 74. Connecting rod 76 being attached to piston 74 operatively connects piston 74 to the other end of reciprocating motor lever arm 66. Limit switch assembly support 78 supports limit switch assembly 80 and limit switch assembly 82 such that the reciprocating motion of reciprocating motor lever arm 66 will energize either limit switch assembly 80 or limit switch assembly 82 depending on the relative volume of dialysate effluent in the fluid chambers aforementioned. Sensor-control instrumentation conductor 54 discussed previously comprises four-way value assembly control conductor 54a, reciprocating motor control conductor 54b, limit switch assembly sensing conductor 54c and limit switch assembly sensing conductor 54d as shown in FIG. 3a. For purposes of illustration, ultrafiltration rate control unit 46 is depicted in FIG. 3. All of the aforementioned instrumentation conductors are connected to ultrafiltration rate control unit 46. More details concerning the operation of the elements in FIG. 3 will be discussed hereinafter in the "Statement of the Operation."

Figure 4:
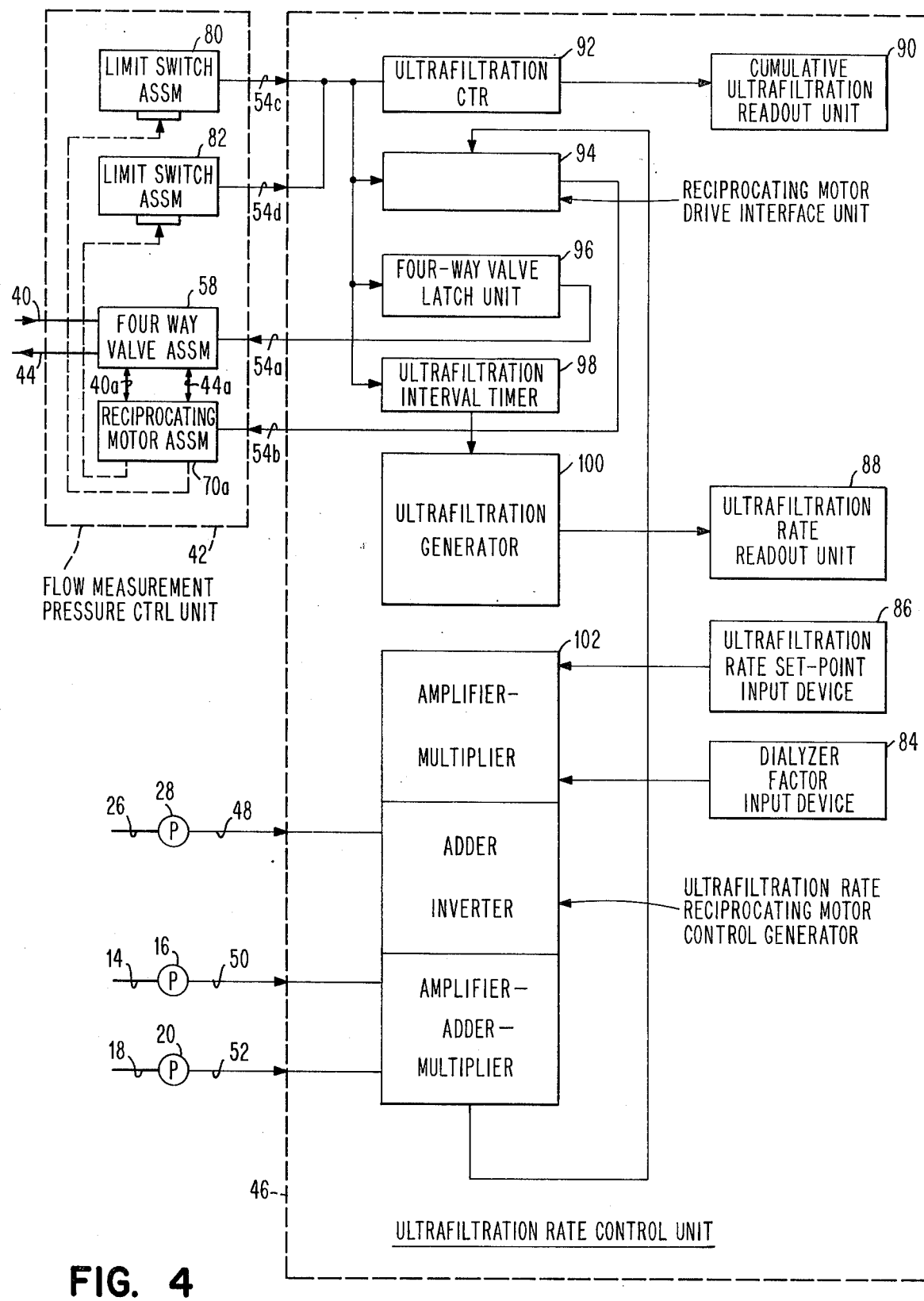
FIG. 4 is a block diagram representation of the elements of the ultrafiltration rate control unit and a block diagram representation of the flow measurement pressure control unit depicting in detail the interface connections between the aforementioned units and the interface with the embodiments of FIGS. 1a and 1b.

Referring now to FIG. 4, a block diagram representation of the elements of ultrafiltration rate control unit 46, flow measurement pressure control unit 42, the interface connections therebetween and the interface connections with other elements of the systems of FIGS. 1a and 1b described hereinbefore is shown. Referring first to flow measurement pressure control unit 42, reciprocating motor assembly 70a which is a block diagram representation of the fluid chambers, pistons, lever arm and motor depicted in FIG. 3, previously described, is operatively connected to limit switch assemblies 80 and 82. Continuing, ultrafiltration rate control unit 46 includes, inter alia, dialyzer factor input device 84, ultrafiltration rate set-point input device 86, ultrafiltration rate readout unit 88 and cumulative ultrafiltration readout unit 90. A signal, representative of switch closures from limit switch assemblies 80 and 82, via limit switch assembly sensing conductors 54c and 54d, respectively, drives ultrafiltration counter 92. The output of the aforementioned counter, which is representative of the total ultrafiltration, drives cumulative ultrafiltration readout unit 90 aforementioned. Connected in parallel to ultrafiltration counter 92 are reciprocating motor drive interface unit 94, four-way valve latch unit 96 and ultrafiltration interval timer 98. Four-way valve latch unit 96 conditions the signal representative of the aforementioned switch closures thereby latching solenoid operated four-way valve 58 via four-way valve control conductor 54a in one of two positions (see FIG. 3). Also, ultrafiltration interval timer 98 conditions the signal representative of the switch closures and, in turn, drives ultrafiltration generator 100. For purposes of the invention, ultrafiltration generator 100 is a device capable of generating a signal representative of the time interval between the switch closures, aforementioned, and inverting same. After inversion, the signal produced is multiplied by an interval signal of constant level which is representative of the volume of fluid chambers 60 and 72 (see FIG. 3). This signal, in turn, is outputted to ultrafiltration rate readout unit 88. The readout depicted is an actual representation of ultrafiltration rate.

Still referring to FIG. 4, a signal representative of the filtration characteristics of a specific dialyzer used is inputted to an ultrafiltration rate reciprocating motor control generator 102 by means of a dialyzer factor input device 84. For purposes of the invention, dialyzer factor input device 84 can be simply a voltage source or a current source and potentiometer combination which can be tuned by an operator. Also, a signal representative of the desired volumetric flow or ultrafiltration rate is inputted to ultrafiltration rate reciprocating motor control generator 102 from ultrafiltration rate set-point input device 86. For purposes of the invention, ultrafiltration rate set-point input device 86 can be a voltage source or a current source and a potentiometer combination which can be tuned by an operator. As depicted in FIG. 4, the aforementioned analog signals, drive the amplifier-multiplier section of ultrafiltration rate reciprocating motor control generator 102. Therein the aforementioned signals are amplified and multiplied driving, in turn, the adder-inverter section of ultrafiltration rate reciprocating motor control generator 102. Also driving the adder-inverter section is a signal representative of the pressure on dialysate supply pressure instrumentation conductor 48. Therein, the aforementioned signals are added and inverted, driving, in turn, the amplifier-adder-multiplier section of ultrafiltration rate reciprocating motor control generator 102. Also, signals representative of the pressure at blood supply pressure instrumentation conductor 50 and blood return pressure instrumentation conductor 52 drive the aforementioned amplifier-adder-multiplier. Consequently, the output of ultrafiltration rate reciprocating motor control generator 102 is an analog signal which drives reciprocating motor drive interface unit 94. For purposes of the invention, reciprocating motor drive interface unit is an amplifier which switches polarity when there is a switch closure of limit switch assembly 80 or 82 and provides a current signal to the torque reciprocating motor 70. The output of reciprocating motor drive interface unit 94 is connected to reciprocating motor assembly 70a. This current signal acts to drive the reciprocating motor therein in a reciprocating fashion, depending on the polarity of the drive signal, thereby providing a braking action to retard movement of the pistons and thus control system pressure (see FIG. 3).

Figure 5:
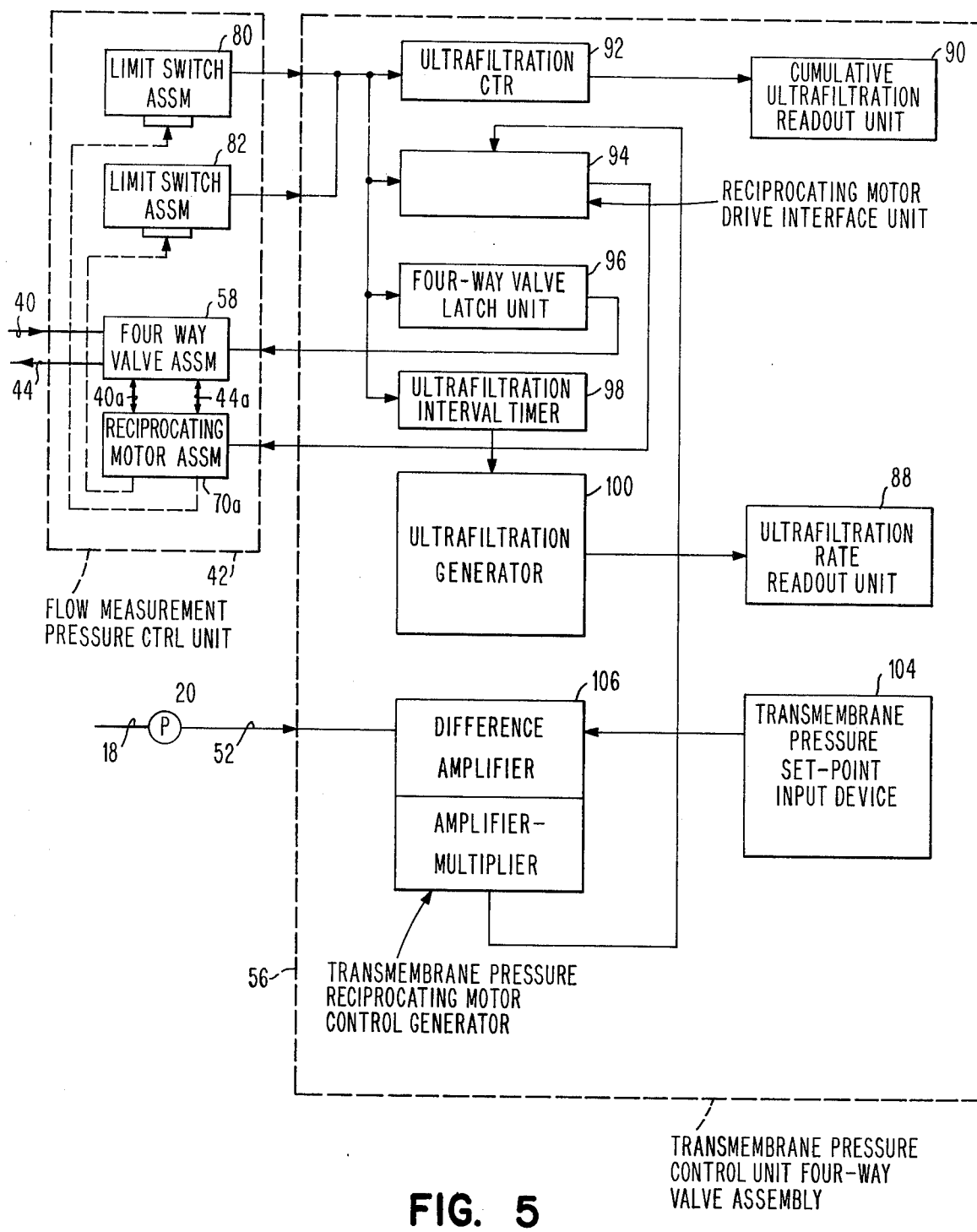
FIG. 5 is a block diagram representation of the elements of transmembrane pressure control unit and a block diagram representation of the flow measurement pressure control unit depicting in detail the interface connections between the aforementioned units and the interface with the embodiments of FIGS. 2a and 2b.

Referring now to FIG. 5, a block diagram representation of the transmembrane pressure control unit 56, the flow measurement pressure control unit 42, the interface connections therebetween and the interface connection with the systems of FIGS. 2a and 2b is shown. In the figure, transmembrane pressure set-point input device 104 provides a signal representative of a desired pressure differential across semipermeable membrane 12 (see FIGS. 2a and 2b). For purposes of the invention, transmembrane pressure set-point input device 104 can be a voltage source or current source and a potentiometer combination which can be tuned by an operator. The signal desired is connected to the difference-amplifier section of transmembrane pressure reciprocating motor control generator 106. Also connected thereto is a signal representative of the pressure at blood return pressure instrumentation conductor 52. Thus, a difference signal is produced and multiplied in the amplifier-multiplier section by an interval signal of constant level which is representative of the area of surfaces 62a and 74a, the length of reciprocating motor lever arm 66 and the torque characteristics of reciprocating motor 70 (see FIG. 3). This resulting signal drives reciprocating motor drive interface unit 94. The remaining elements and the connections thereof are the same as previously described in FIG. 4.

STATEMENT OF THE OPERATION

Details of the operation, according to the invention, are explained in conjunction with FIGS. 1a, 3, and 4 viewed concurrently.

At the start of hemodialysis treatment, an operator using dialyzer factor input device 84 tunes in a signal which is representative of constant and known filtration characteristics of semipermeable membrane 12. Also, based on medical and physical characteristics of the patient to be treated, an operator using ultrafiltration rate set-point input device 86 tunes in a desired ultrafiltration rate. This signal, and the previous signal, feed the amplifier-multiplier section of ultrafiltration rate reciprocating motor control generator 102. Blood from the patient is transported into the blood side of sealed dialyzer 10 via blood supply line 14. A blood supply pressure sensing device 16, connected thereto, senses the blood pressure and converts it into an electrical signal which feeds the amplifier-adder-multiplier section of ultrafiltration rate reciprocating motor control generator 102. A dialysate supply constant volume displacement pump 24 pumps dialysate into the dialysate side of sealed dialyzer 10 via dialysate supply line 26. Dialyzer supply pressure sensing device, connected to the afore-mentioned line, senses the pressure and converts it into an electrical signal. This signal is fed into the adder inverter section of ultrafiltration rate reciprocating motor control generator 102.

Still referring to FIGS. 1a, 3, and 4, blood is returned to the patient via blood return line 18. The blood pressure in the afore-mentioned line is sensed by blood return pressure sensing device 20 and converted into an electrical signal. This signal is also fed to the amplifier-adder-multiplier section of ultrafiltration rate reciprocating motor control generator 102. With the aforementioned signal present, an electrical current, which is proportional to torque and having a value dependent on system parameters and the desired ultrafiltration rate, drives reciprocating motor drive interface unit 94, thereby applying the correct drive current to reciprocating motor 70 via reciprocating motor control conductor 54b.

A dialyzer effluent constant volume displacement pump 34 pumps dialysate effluent from sealed dialyzer 10 via dialyzer effluent inlet line 32. The performance characteristics of dialysate supply constant volume displacement pump 24, aforementioned, and dialyzer effluent constant volume displacement pump 34 are similar. Accordingly, the volume of dialysate pumped into the system by dialysate supply constant volume displacement pump 24 is equal to the volume of dialysate effluent pumped into effluent receptacle 38. Thus, a volume of dialysate effluent equivalent to the volume of ultrafiltrate is routed to flow measurement pressure control unit 42. Since this is a closed dialysate flow system, the ultrafiltrate is the actual fluid volume of water and other impurities removed from the blood of the patient under treatment. Continuing, as dialysate effluent enters fluid chamber 60, a pressure head is built up against surface 62a of piston 62. The filling of fluid chamber 60 with dialysate 60a represents a fixed and known fluid volume. Thus, when the fluid in fluid chamber 60 reaches the fixed volume (see FIG. 3), reciprocating motor lever arm 68, being operatively connected to piston 62, activates limit switch assembly 80 producing a switch closure and a signal thereby (two switch closures represent a fixed volume of dialysate effluent). At this time, the signal, representative of the switch closure, drives ultrafiltration counter 92, reciprocating motor driver interface unit 94, four-way valve latch unit 96 and ultrafiltration interval timer 98, concurrently. Accordingly, ultrafiltration counter 92 counts the switch closures over the period of treatment and drives cumlative ultrafiltration readout unit 90. For purposes of the invention, cumulative ultrafiltration readout unit 90 can be a printer which simply prints the total number of switch closures which is directly proportional to the volume of ultrafiltrate. The actual volume of ultrafiltrate removed from a patient under treatment could then be displayed on a LED readout unit or similar device (subject to designer'schoice). s choice).

In addition, when there is a switch closure, reciprocating motor 70 is reversed by reciprocating motor drive interface unit 94 which reverses the direction of the current on reciprocating motor control conductor 54d. Also, four-way valve latch unit 96 activates four-way valve assembly 58 so that fluid exits from fluid chamber 60 and fluid chamber 72 begins to fill. As the hemodialysis treatment continues, fluid chamber 72 fills with dialysate effluent forming a pressure head on surface 74a of piston 74 which cooperates with reciprocating lever arm 66 forcing it against limit switch assembly 82. At this time, the process is reversed again.

It should be noted, that the pressure in the aforementioned fluid chambers is proportional to the amount of torque applied by reciprocating motor 70 to reciprocating motor lever arm 66. The rate of filling of these fluid chambers is directly proportional to the ultrafiltration rate. It should also be noted that the torque provided by reciprocating motor 70 is directly proportional to the current in reciprocating motor control conductor 54b. Thus, the retarding force on fluid chambers 60 and 72 controls pressure of dialysate effluent lines 40, 30 and 32, and accordingly, system pressure and ultrafiltration rate.

Finally, since ultrafiltration rate is measured in volume per unit time, the ultrafiltration rate is computed by applying the signals representative of the switch closures of limit switch assemblies 80 and 82 to ultrafiltration interval timer 98, which provides a signal indicative of the time between switch closures. This signal in turn, drives ultrafiltration generator 100, which inverts the signal and multiplies it by a constant signal which is proportional to the volume of fluid chamber 60 or fluid chamber 70. Thus, ultrafiltration generator 100 provides a signal equivalent to ultrafiltration rate. This signal, in turn, drives ultrafiltration rate readout unit 88, which for purposes of the invention, is substantially the same as cumulative ultrafiltration readout unit 90 aforementioned.

It should be noted that the oncotic pressure effects of the blood and the osmotic pressure effects of the dialysate solution were not directly included in this invention because they are constants which can be included in both control units 46 and 56.

While the invention has been particularly described with reference to the preferred embodiments thereof, without correction for the oncotic pressure of the blood, it will be understood by those skilled in the art that various changes in form and detail may be made therein without departing from the spirit and scope of the invention.

What is claimed is:

1. An automated hemodialysis treatment system for controlling ultrafiltration rate to a preset value, measuring said ultrafiltration rate, and measuring the total quantity of ultrafiltrate removed from a patient under treatment comprising:

a sealed dialyzer separated into a blood side and a dialysate side by a semipermeable membrane having constant and known filtration characteristics for removing water and impurities from the blood;

a blood supply line connected to said blood side of said dialyzer for supplying blood to be treated from said patient under treatment;

blood supply pressure sensing means connected to said blood supply line for sensing the pressure of said blood to be treated and for converting said pressure of said blood to be treated into an electrical signal;

a blood return line connected to said blood side of said dialyzer for returning treated blood to said patient under treatment;

blood return pressure sensing means connected to said blood return line for sensing the pressure of said treated blood therein; and for converting said pressure of said treated blood into an electrical signal;

a dialysate supply means connected to said dialysate side of said sealed dialyzer via a dialysate supply line for pumping dialysate into said sealed dialyzer; the pumping rate of dialysate entering said dialyzer being the same as the pumping rate of dialysate effluent leaving said dialzyer;

dialysate supply pressure sensing means connected to said dialysate supply line for sensing the pressure of dialysate therein, and for converting said pressure of said dialysate into an electrical signal;

flow measurement pressure control means connected to said dialysate side of said sealed dialyzer via a flow measurement pressure control input line for receiving a quantity of dialysate effluent equivalent to the amount of ultrafiltrate removed from the blood through said semipermeable membrane, and for controlling the fluid pressure and simultaneously metering the fluid flow therethrough; said dialysate effluent, in turn, being routed via a flow measurement pressure control output line to a dialysate effluent receptacle;

said flow measurement pressure control means being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of the two fluid chambers receiving and transmitting a known volume of dialysate effluent at alternate times; the pistons in each of said at least two fluid chambers providing a bias force against the filling of the two fluid chambers; a reciprocating motor for supporting an arm that is operably connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and ultrafiltration rate control means operatively connected to said flow measurement pressure control means via a sensor-control instrumentation conductor and said ultrafiltration rate control means also being operatively connected to said electrical signal of said blood supply pressure sensing means, said electrical signal of said blood return pressure sensing means and said electrical signal of said dialysate supply pressure sensing means for controlling said ultrafiltration rate to a preset value, measuring said ultrafiltration rate and said total quantity of ultrafiltrate removed from said patient under treatment.

2. An automated hemodialysis treatment single pass dialysate system for controlling ultrafiltration rate to a preset value, measuring said ultrafiltration rate, and measuring the total quantity of ultrafiltrate removed from a patient uder treatment comprising:

a sealed dialyzer separated into a blood side and a dialysate side by a semipermeable membrane having constant and known filtration characteristics for removing water and impurities from the blood;

a blood supply line connected to said blood side of said dialyzer for supplying blood to be treated from said patient under treatment;

blood supply pressure sensing means connected to said blood supply line for sensing the pressure of said blood to be treated and for converting said pressure of said blood to be treated into an electrical signal;

a blood return line connected to said blood side of said dialyzer for returning treated blood to said patient under treatment;

blood return pressure sensing means connected to said blood return line for sensing the pressure of said treated blood therein, and for converting said pressure of said treated blood into an electrical signal;

a dialysate supply constant volume displacement pump connected to said dialysate side of said sealed dialyzer via a dialysate supply line and connected to a source of dialysate via a dialysate pump supply line for pumping said dialysate into said sealed dialyzer;

dialysate supply pressure sensing means connected to said dialysate supply line for sensing the pressure of dialysate therein, and for converting said pressure of said dialysate into an electrical signal;

a dialyzer effluent constant volume displacement pump connected to said dialysate side of said sealed dialyzer via a dialyzer effluent pump inlet line for pumping dialysate effluent from said sealed dialyzer to a dialyzer effluent pump outlet line; the pumping rate of said dialysate supply constant volume displacement pump being the same as the pumping rate of said dialyzer effluent constant volume displacement pump;

an effluent receptacle connected to said dialyzer effluent pump inlet line for receiving said dialysate effluent;

flow measurement pressure control means connected to said dialysate side of said sealed dialyzer via a flow measurement pressure control input line for receiving a quantity of said dialysate effluent equivalent to the amount of ultrafiltrate removed from the blood through said semipermeable membrane, and for controlling the fluid pressure and simultaneously metering the fluid flow therethrough; said dialysate effluent, in turn, being routed via a flow measurement pressure control output line to said effluent receptacle;

said flow measurement pressure control means being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of the two fluid chambers receiving and transmitting a known volume of dialysate effluent at alternate times; the pistons in each of said at least two fluid chambers providing a bias force against the filling of the two fluid chambers; a reciprocating motor for supporting an arm that is operatively connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and ultrafiltration rate control means operably connected to said flow measurement pressure control means via a sensor-control instrumentation conductor and said ultrafiltration rate control means also being operatively connected to said electrical signal of said blood supply pressure sensing means, said electrical signal of said blood return pressure sensing means and said electrical signal of said dialysate supply pressure sensing means for controlling said ultrafiltration rate to a present value, measuring said ultrafiltration rate and said total quantity of ultrafiltrate removed from said patient under treatment.

3. An automated hemodialysis treatment single pass dialysate system as set forth in claim 2 wherein said ultrafiltration rate control means comprises:

an ultrafiltration rate reciprocating motor control generator being operatively connected to receive said electrical signal from said blood supply pressure sensing means, said electrical signal from said blood return pressure sensing means and said electrical signal from said dialysate supply pressure sensing means;

a dialyzer factor input device for transferring a signal representative of the constant and known filtration characteristics of said semipermeable means to said ultrafiltration rate reciprocating motor control generator;

an ultrafiltration rate set-point input device for supplying a signal to said ultrafiltration rate reciprocating motor control generator that is representative of the desired ultrafiltration rate;

an ultrafiltration counter for receiving a signal representative of the amount of dialysate effluent passing through said flow measurement pressure control means; said signal being determined by the number of switch activations of said switching means;

a cumulative ultrafiltration readout unit for displaying the amount of dialysate effluent passing through said flow measurement pressure control means;

a motor drive interface unit connected in parallel to said ultrafiltration counter and receiving an output signal from said ultrafiltration rate reciprocating motor control generator, the output of said motor drive interface unit controlling said reciprocating motor;

a four-way valve latch unit connected in parallel to said ultrafiltration counter for conditioning said signal representative of the number of switch activations of said switching means, and thereby latching said valve means;

an ultrafiltration interval timer connected in parallel to said ultrafiltration counter for conditioning said signal representative of the number of switch activations of said switching means;

an ultrafiltration generator connected to said ultrafiltration timer for receiving said conditioned signal, to thereby generate a signal representative of the time interval between the activation of the at least two switches, and equivalent to ultrafiltration rate; and an ultrafiltration rate readout unit for displaying ultrafiltration rate.

4. An automated hemodialysis treatment recirculating dialysate system for controlling ultrafiltration rate to a present value, measuring said ultrafiltration rate, and measuring the total quantity of ultrafiltrate removed from a patient under treatment comprising:

a sealed dialyzer separated into a blood side and a dialysate side by a semipermeable membrane having constant and known filtration characteristics for removing water and impurities from the blood;

a blood supply line connected to said blood side of said dialyzer for supplying blood to be treated from said patient under treatment;

blood supply pressure sensing means connected to said blood supply line for sensing the pressure of said blood to be treated, and for converting said pressure of said blood to be treated into an electrical signal;

a blood return line connected to said blood side of said dialyzer for returning treated blood to said patient under treatment;

blood return pressure sensing means connected to said blood return line for sensing the pressure of said treated blood therein, and for converting said pressure of said treated blood into an electrical signal;

a dialysate circulator connected to said dialysate side of said sealed dialyzer via a dialysate supply line for circulating dialysate through said sealed dialyzer;

dialysate supply pressure sensing means connected to said dialysate supply line for sensing the pressure of dialysate therein, and for converting said pressure of said dialysate into an electrical signal;

a dialysate effluent return line having one end connected to said dialysate side of said sealed dialyzer and the other end connected to said dialysate circulator for transporting dialysate effluent from said sealed dialyzer to said dialysate circulator;

flow measurement pressure control means connected to said dialysate side of said sealed dialyzer via a flow measurement pressure control input line for receiving a quantity of said dialysate effluent equivalent to the amount of ultrafiltrate removed from the blood through said semipermeable membrane, and for controlling the fluid pressure and simultaneously metering the fluid flow therethrough; an effluent receptacle connected to said flow measurement pressure control means by a flow measurement pressure control output line for receiving dialysate effluent routed therefrom;

said flow measurement pressure control means being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of the two fluid chambers receiving and transmitting a known volume of dialysate effluent at alternate times; the pistons in each of said at least two fluid chambers providing a bias force against the filling of the two fluid chambers; a reciprocating motor for supporting an arm that is operatively connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and ultrafiltration rate control means operatively connected to said flow measurement pressure control means via a sensor-control instrumentation conductor and said ultrafiltration rate control means also being operable connected to said electrical signal of said blood supply pressure sensing means, said electrical signal of said blood return pressure sensing means and said electrical signal of said dialysate supply pressure sensing means for controlling said ultrafiltration rate to a preset value, measuring said ultrafiltration rate and said total quantity of ultrafiltrate removed from said patient under treatment.

5. An automated hemodialysis treatment recirculating dialysate system as set forth in claim 4 wherein said dialysate circulator comprises:
 a fixed volume dialysate reservoir connected to said dialysate effluent return line for receiving said dialysate effluent from said sealed dialyzer, and connected to a dialysate pump supply line for supplying dialysate to said sealed dialyzer; and
 a dialysate recirculating pump having an inlet connected to said dialysate pump supply line and an outlet connected to said dialysate supply line for pumping dialysate to said sealed dialyzer and for circulating dialysate effluent to said fixed volume dialysate reservoir.

6. An automated hemodialysis treatment recirculating dialysate system as set forth in claim 4 wherein said ultrafiltration rate control means comprises:
 an ultrafiltration rate reciprocating motor control generator being operatively connected to receive said electrical signal from said blood supply pressure sensing means, said electrical signal from said blood return pressure sensing means and said electrical signal from said dialysate supply pressure sensing means;
 a dialyzer factor input device for transferring a signal representative of the constant and known filtration characteristics of said semipermeable means to said ultrafiltration rate reciprocating motor control generator;
 an ultrafiltration rate set-point input device for supplying a signal to said ultrafiltration rate reciprocating motor control generator that is representative of the desired ultrafiltration rate;
 an ultrafiltration counter for receiving a signal representative of the amount of dialysate effluent passing through said flow measurement pressure control means; said signal means being determined by the number of switch activations of said switching means;
 a cumulative ultrafiltration readout unit for displaying the amount of dialysate effluent passing through said flow measurement pressure control means;
 a motor drive interface unit connected in parallel to said ultrafiltration counter and receiving an output signal from said ultrafiltration rate reciprocating motor control generator, the output of said motor drive interface unit controlling said reciprocating motor;
 a four-way valve latch unit connected in parallel to said ultrafiltration counter for conditioning said signal representative of the number of switch activations of said switching means, and thereby latching said valve means;
 an ultrafiltration interval timer connected in parallel to said ultrafiltration counter for conditioning said signal representative of the number of switch activations of said switching means;
 an ultrafiltration generator connected to said ultrafiltration timer for receiving said conditioned signal, to thereby generate a signal representative of the time interval between the activation of the at least two switches, and equivalent to ultrafiltration rate; and
 an ultrafiltration rate readout unit for displaying ultrafiltration rate.

7. An atomated hemodialysis treatment system for controlling transmembrane pressure to a preset value, measuring said ultrafiltration rate, and measuring the total quantity of ultrafiltrate removed from a patient under treatment comprising:
 a sealed dialyzer separated into a blood side and a dialysate side by a semipermeable membrane having filtration characteristics that are not constant and known for removing water and impurities from the blood;
 a blood supply line connected to said blood side of said dialyzer for supplying blood to be treated from said patient under treatment;
 a blood return line connected to said blood side of said dialyzer for returning treated blood to said patient under treatment;
 blood return pressure sensing means connected to said blood return line for sensing the pressure of said treated blood therein, and for converting said pressure of said treated blood into an electrical signal;
 a dialysate supply means connected to said dialysate side of said sealed dialyzer via a dialysate supply line for pumping dialysate into said sealed dialyzer; the pumping rate of dialysate entering said dialyzer being the same as the pumping rate of dialysate effluent leaving said dialyzer;
 flow measurement pressure control means connected to said dialysate side of said sealed dialyzer via a flow measurement pressure control input line for receiving a quantity of dialysate effluent equivalent to the amount of ultrafiltrate removed from the blood through said semipermeable membrane, and for controlling the fluid pressure and simultaneously metering the fluid flow therethrough; said dialysate effluent, in turn, being routed via a flow measurement pressure control output line to a dialysate effluent receptacle;
 said flow measurement pressure control means being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of the two fluid chambers receiving and transmitting a known volume of dialysate effluent at alternate times; the pistons in each of said at least two fluid members providing a bias force against the filling of the two fluid chambers; a reciprocating motor for supporting an arm that is operatively connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and
 transmembrane pressure control means operable connected to said flow measurement pressure control means via a sensor-control instrumentation conductor of said transmembrane pressure control means also being operatively connected to said electrical signal of said blood return pressure sensing means for controlling said transmembrane pressure to a preset value, measuring said ultrafiltration rate and said total quantity of ultrafiltrate removed from said patient under treatment.

8. An automated hemodialysis treatment single pass dialysate system for controlling transmembrane pressure to a preset value, measuring said ulrafiltration rate, and measuring the total quantity of ultrafiltrate removed from a patient under treatment comprising:

a sealed dialyzer separated into a blood side and a dialysate side by a semipermeable membrane having filtration characteristics that are not constant and known for removing water and impurities from the blood;

a blood supply line connected to said blood side of said dialyzer for supplying blood to be treated from said patient under treatment;

a blood return line connected to said blood side of said dialyzer for returning treated blood to said patient under treatment;

blood return pressure sensing means connected to said blood return line for sensing the pressure of said treated blood therein, and for converting said pressure of said treated blood into an electrical signal;

a dialysate supply constant volume displacement pump connected to said dialysate side of said sealed dialyzer via a dialysate supply line and connected to a source of dialysate via a dialysate pump supply line for pumping said dialysate into said sealed dialyzer;

a dialyzer effluent constant volume displacement pump connected to said dialysate side of said sealed dialyzer via a dialyzer effluent pump inlet line for pumping dialysate effluent from said sealed dialyzer to a dialyzer effluent pump outlet line; the pumping rate of said dialysate supply constant volume displacement pump being the same as the pumping rate of said dialyzer effluent constant volume displacement pump;

an effluent receptacle connected to said dialyzer effluent pump outlet line for receiving said dialysate effluent;

flow measurement pressure control means connected to said dialysate side of said sealed dialyzer via a flow measurement pressure control input line for receiving a quantity of said dialysate effluent equivalent to the amount of ultrafiltrate removed from the blood through said semipermeable membrane, and for controlling the fluid pressure and simultaneously metering the fluid flow therethrough, said dialysate effluent, in turn, being routed via a flow measurement pressure control output line to said effluent receptacle;

said flow measurement pressure control meams being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of the two fluid chambers receiving and transmitting a known volume of dialysate effluent at alternate times; the pistons in each of said at least two fluid chambers providing a bias force against the filling of the two fluid chambers; a reciprocating motor for supporting an arm that is operatively connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and transmembrane pressure control means operably connected to said flow measurement pressure control means via a sensor-control instrumentation conductor and said transmembrane pressure control means also being operatively connected to said electrical signal of said blood return pressure sensing means for controlling said transmembrane pressure to a preset value, measuring said ultrafiltration rate and said total quantity of ultrafiltrate removed from said patient under treatment.

9. An automated hemodialysis treatment single pass dialysate system as set forth in claim 8 wherein said transmembrane pressure control means comprises:

a transmembrane pressure reciprocating motor control generator being operably connected to receive said electrical signal from said blood return pressure sensing means;

a transmembrane pressure set-point input device connected to said transmembrane pressure reciprocating motor control generator for supplying a signal to said transmembrane pressure reciprocating motor control gennerator that is representative of the desired pressure differential across said semipermeable membrane;

an ultrafiltration counter for receiving a signal representative of the amount of dialysate effluent passing through said flow measurement pressure control means; said signal being determined by the number of switch activations of said switching means;

a cumulative ultrafiltration readout unit for displaying the amount of dialysate effluent passing through said flow measurement pressure control means;

a motor drive interface unit connected in parallel to said ultrafiltration counter and receiving an output signal from said transmembrane pressure reciprocating motor control generator, the output of said motor drive interface unit controlling said reciprocating motor;

a four-way valve latch unit connected in parallel to said ultrafiltration counter for conditioning said signal representative of the number of switch activations of said switching means, and thereby latching said valve means;

an ultrafiltration interval timer connected in parallel to said ultrafiltration counter for conditioning said signal representative of the number of switch activations of said switching means;

an ultrafiltration generator connected to said ultrafiltration timer for receiving said conditioned signal, to thereby generate a signal representative of the time interval between the activation of the at least two switches, and equivalent to ultrafiltration rate; and an ultrafiltration rate readout unit for displaying ultrafiltration rate.

10. An automated hemodialysis treatment recirculating dialysate system for controlling transmembrane pressure to a preset valve, measuring said ultrafiltration rate, and measuring the total quantity of ultrafiltrate removed from a patient under treatment comprising:

a sealed dialyzer separated into a blood side and a dialysate side by a semipermeable membrane having filtration characteristics that are not constant and known for removing water and impurities from the blood;

a blood supply line connected to said blood side of said dialyzer for supplying blood to be treated from said patient under treatment;

a blood return line connected to said blood side of said dialyzer for returning treated blood to said patient under treatment;

blood return pressure sensing means connected to said blood return line for sensing the pressure of said treated blood therein, and for converting said pressure of said treated blood into an electrical signal;

a dialysate circulator connected to said dialysate side of said sealed dialyzer via dialysate supply line for circulating dialysate through said sealed dialyzer;

a dialysate effluent return line having one end connected to said dialysate side of said sealed dialyzer and the other end connected to said dialysate circulator for transporting dialysate effluent from said sealed dialyzer to said dialysate circulator;

flow measurement pressure control means connected to said dialysate side of said sealed dialyzer via a flow measurement pressure control input line for receiving a quantity of said dialysate effluent equivalent to the amount of ultrafiltrate removed from the blood through said semipermeable membrane, and for controlling the fluid pressure and simultaneously metering the fluid flow therethrough; an effluent receptacle connected to said flow measurement pressure control means by a flow measurement pressure control output line for receiving dialysate effluent routed therefrom;

said flow measurement pressure control means being comprised of valve means for controlling the flow of said dialysate effluent through said flow measurement pressure control input line into said flow measurement pressure control means, and for controlling the flow of said dialysate effluent out of said flow measurement pressure control means and into said flow measurement pressure control output line; at least two fluid chambers with pistons therein connected to said valve means with each of two fluid chambers receiving and transmitting a known volume of dialysate effluent at alternate times; the pistons in each of said at least two fluid chambers providing a bias force against the filling of the two fluid chambers; a reciprocating motor for supporting an arm that is operatively connected to the pistons at ends that are opposite the ends of the pistons that provide a bias force against the filling of the fluid chambers; said reciprocating motor providing reciprocating motion to the arm to control the amount of bias force that is imparted to the pistons via the arm to thereby control the pressure in the dialysate system; and switching means comprised of at least two switches that are positioned so as to be activated by the ends of the arm as it is being reciprocated, and with each activation of the switches corresponding to the known volume of dialysate effluent that is received by each of the fluid chambers; and transmembrane pressure control means operably connected to said flow measurement pressure control means via a sensor-control instrumentation conductor and said transmembrane pressure control means also being operatively connected to said electrical signal of said blood return pressure sensing means for controlling said transmembrane pressure to a preset value measuring said ultrafiltration rate and said total quantity of ultrafiltrate removed from said patient under treatment.

11. An automated hemodialysis treatment recirculating dialysate system as set forth in claim 10 wherein said dialysate circulator comprises:

a fixed volume dialysate reservoir connected to said dialysate effluent return line for receiving said dialysate effluent from said sealed dialyzer, and connected to a dialysate pump supply line for supplying dialysate to said sealed dialyzer; and a dialysate recirculating pump having an inlet connected to said dialysate pump supply line and an outlet connected to said dialysate supply line for pumping dialysate to said sealed dialyzer and for circulating dialysate effluent to said fixed volume dialysate reservoir.

12. An automated hemodialysis treatment recirculating dialysate system as set forth in claim 10 wherein said transmembrane pressure control means comprises:

a transmembrane pressure reciprocating motor control generator being operatively connected to receive said electrical signal from said blood return pressure sensing means;

a transmembrane pressure set-point input device connected to said transmembrane pressure reciprocating motor control generator for supplying a signal to said transmembrane pressure reciprocating motor control generator that is representative of the desired pressure differential across said semipermeable membrane;

an ultrafiltration counter for receiving a signal representative of the amount of dialysate effluent passing through said flow measurement pressure control means; said signal being determined by the number of switch activations of said switching means;

a cumulative ultrafiltration readout unit for displaying the amount of dialysate effluent passing through said flow measurement pressure control means;

a motor drive interface unit connected in parallel to said ultrafiltration counter and receiving an output signal from said transmembrane pressure reciprocating motor control generator, the output of said motor drive interface unit controlling said reciprocating motor;

a four-way valve latch unit connected in parallel to said ultrafiltration counter for conditioning said signal representative of the number of switch activations of said switching means, and thereby latching said valve means;

an ultrafiltration interval timer connected in parallel to said ultrafiltration counter for conditioning said signal representative of the number of switch activations of said switching means;

an ultrafiltration generator connected to said ultrafiltration timer for receiving said conditioned signal, to thereby generate a signal representative of the time interval between the activation of the at least two switches, and equivalent to ultrafiltration rate; and an ultrafiltration rate readout unit for displaying ultrafiltration rate.

13. Apparatus for controlling pressure in a fluid system having an input line and an output line and simultaneously measuring fluid flow through said system comprising:

four-way valve means fpr reversing the path of fluid through said input line and said output line;

a first fluid chamber connected to said input line via said four-way valve means for receiving said fluid routed thereto;

a first piston operatively connected to said first fluid chamber, said fluid in said first fluid chamber being compressed against the face of said first piston;

a second fluid chamber connected to said output line via said four-way valve means for receiving said fluid routed thereto;

a second piston operatively connected to said second fluid chamber, said fluid in said second fluid chamber being compressed against the face of said second piston;

a lever arm having a first end thereof operatively connected to said first piston and a second end thereof operatively connected to said second piston;

torque motor means operably connected to the center of said level arm, said torque motor means supplying a braking action for retarding the movement of said first and second pistons, thereby contolling system pressure;

first switch means positioned on a support so as to be activated by said first end of said lever arm when said first piston reaches its stroke limit; and second switch means positioned on said support so as to be activated by said second end of said lever arm when said second piston reaches its stroke limit;

said switch means counting the number of stroke limits of said pistons thereby accounting for the volume of said fluid passing through said system.

14. An automated method of hemodialysis treatment for controlling ultrafiltration rate to a preset value, measuring said ultrafiltration rate, and measuring the total quantity of ultrafiltrate removed from a patient under treatment with a hemodialysis system, comprising the steps of:

selecting an operating rate for the hemodialysis system that is representative of constant and known filtration characteristics of a semipermeable membrane in a dialyzer;

adjusting the ultrafiltration rate based upon the medical and physical characteristics of the patient under treatment;

transporting blood from the patient into an inlet at one side of said dialyzer;

pumping dialysate from a source of dialysate into an inlet at the other side of said dialyzer and then pumping said dialysate, including ultrafiltrate, out of said dialyzer at an outlet on said other side of said dialyzer into a dialyzer effluent receiving means; the pumping rate for fluid entering said outer side of said dialyzer being the same as fluids entering said dialyzer effluent receiving means;

returning said blood from said dialyzer at an outlet on said one side of dialyzer to the patient under treatment;

sensing the pressure of said blood entering said dialyzer, the pressure of said blood leaving said dialyzer and the pressure of said dialysate entering said dialyzer;

routing a volume of dialysate substantially equivalent to the volume of ultrafiltrate leaving said other side of said dialyzer to a flow measurement pressure control unit;

measuring the volume of ultrafiltrate passing through said flow measurement pressure control unit in at least two fluid chambers of known volume that are alternately emptied and filled;

controlling fluid pressure in said flow measurement pressure control unit and in the hemodialysis system by controlling the amount of pressure that is placed upon the ultrafiltrate as it passes through said flow measurement pressure control unit;

comparing the pressures of fluids entering the exiting said dialyzer with the volume of ultrafiltrate passing through said flow measurement pressure control unit;

generating a signal proportional to the volume of ultrafiltrate leaving said flow measurement pressure control unit, and measuring the rate at which said ultrafiltrate leaves said flow mesurement pressure control unit.

15. An automated method of hemodialysis treatment for controlling ultrafiltration rate to a preset value, measuring said ultrafiltration rate, and measuring the total quantity of ultrafiltrate removed from a patient under treatment with a hemodialysis system, configurated in a single pass dialysate system, comprising the steps of:

selecting an operating rate for the hemodialysis system that is representative of constant and known filtration characteristics of a semipermeable membrane in a dialyzer;

adjusting the ultrafiltration rate based upon the medical and physical characteristics of the patient under treatment;

transporting blood from the patient into an inlet at one side of said dialyzer;

pumping dialysate from a source of dialysate into an inlet at the other side of said dialyzer and then pumping said dialysate, including ultrafiltrate, out of said dialyzer at an outlet on said other side of said dialyzer into an effluent receptacle; the pumping rate for fluid entering said other side of said dialyzer being the same as fluids entering said effluent receptacle;

returning said blood from said dialyzer at an outlet on said one side of dialyzer to the patient under treatment;

sensing the pressure of said blood entering said dialyzer, the pressure of said blood leaving said dialyzer and the pressure of said dialysate entering said dialyzer;

routing a volume of dialysate substantially equivalent to the volume of ultrafiltrate leaving said other side of said dialyzer to a flow measurement pressure control unit;

measuring the volume of ultrafiltrate passing through said flow measurement pressure control unit in at least two fluid chambers of known volume that are alternately emptied and filled before passing the ultrafiltrate on to said effluent receptacle;

controlling fluid pressure in said flow measurement pressure control unit and in the hemodialysis system by controlling the amount of pressure that is placed upon the ultrafiltrate as it passes through said flow measurement pressure control unit;

comparing the pressures of fluids entering the exiting said dialyzer with the volume of ultrafiltrate passing through said flow measurement pressure control unit;

generating a signal proportional to the volume of ultrafiltrate leaving said flow measurement pressure control unit, and measuring the rate at which said ultrafiltrate leaves said flow measurement pressure control unit.

16. An automated method of hemodialysis treatment for controlling ultrafiltration rate to a preset value, measuring said ultrafiltration rate, and measuring the total quantity of ultrafiltrate removed from a patient under treatment with a hemodialysis system, configurated in a recirculating dialysate system, comprising the steps of:

selecting an operating rate for the hemodialysis system that is representative of constant and known filtration characteristics of a semipermeable membrane in a dialyzer;

adjusting the ultrafiltration rate based upon the medical and physical characteristics of the patient under treatment;

transporting blood from the patient into an inlet at one side of said dialyzer;

pumping dialysate from a source of fixed volume dialysate into an inlet at the other side of said dialyzer and then pumping said dialysate, including ultrafiltrate, out of said dialyzer at an outlet on said other side of said dialyzer back into said source of dialysate; the pumping rate for fluid entering said other side of said dialyzer being the same as fluids entering said source of dialysate;

returning said blood from said dialyzer at an outlet on said one side of said dialyzer to the patient under treatment;

sensing the pressure of said blood entering said dialyzer, the pressure of said blood leaving said dialyzer and the pressure of said dialysate entering said dialyzer;

routing a volume of dialysate substantially equivalent to the volume of ultrafiltrate leaving said other side of said dialyzer to a flow measurement pressure control unit;

measuring the volume of ultrafiltrate passing through said flow measurement pressure control unit in at least two fluid chambers of known volume that are alternately emptied and filled before passing the ultrafiltrate on to an effluent receptacle;

controlling fluid pressure in said flow measurement pressure control unit and in the hemodialysis system by controlling the amount of pressure that is placed upon the ultrafiltrate as it passes through said flow measurement pressure control unit;

comparing the pressures of fluids entering and exiting said dialyzer with the volume of ultrafiltrate passing through said flow measurement pressure control unit;

generating a signal proportional to the volume of ultrafiltrate leaving said flow measurement pressure control unit, and measuring the rate at which said ultrafiltrate leaves said flow measurement pressure control unit.

17. An automated method of hemodialysis treatment for controlling transmembrane pressure to a preset value, measuring said ultrafiltration rate, and measuring the total quantity of ultrafiltrate removed from a patient under treatment with a hemodialysis system, comprising the steps of:

selecting an operating pressure across a semipermeable membrane in a dialyzer;

transporting blood from the patient into an inlet at one side of said dialyzer;

pumping dialysate from a source of dialysate into an inlet at the other side of said dialyzer and then pumping said dialysate, including ultrafiltrate, out of said dialyzer at an outlet on said other side of said dialyzer into a dialyzer effluent receiving means; the pumping rate for fluid entering said other side of said dialyzer being the same as fluids entering said dialyzer effluent receiving means;

returning said blood from said dialyzer at an outlet on said one side of said dialyzer to the patient under treatment;

sensing the pressure of said blood leaving said dialyzer;

routing a volume of dialysate substantially equivalent to the volume of ultrafiltrate leaving said other side of said dialyzer to a flow measurement pressure control unit;

measuring the volume of ultrafiltrate passing through said flow measurement pressure control unit in at least two fluid chambers of known volume that are alternately emptied and filled;

controlling fluid pressure in said flow measurement pressure control unit and in the hemodialysis system by controlling the amount of pressure that is placed upon the ultrafiltrate as it passes through said flow measurement pressure control unit;

comparing the pressure of blood exiting said dialyzer with the volume of ultrafiltrate passing through said flow measurement pressure control unit;

generating a signal proportional to the volume of ultrafiltrate leaving said flow measurement pressure control unit, and measuring the rate at which said ultrafiltrate leaves said flow measurement pressure control unit.

18. An automated method of hemodialysis treatment for controlling transmembrane pressure to a preset value, measuring said ultrafiltration rate, and measuring the total quantity of ultrafiltrate removed from a patient under treatment with a hemodialysis system configurated in a single pass dialysate system, comprising the steps of:

selecting an operating pressure across a semipermeable membrane in a dialyzer;

transporting blood from the patient into an inlet at one side of said dialyzer;

pumping dialysate from a source of dialysate into an inlet at the other side of said dialyzer and then pumping said dialysate, including ultrafiltrate, out of said dialyzer at an outlet on said other side of said dialyzer into an effluent receptacle; the pumping rate for fluid entering said other side of said dialyzer being the same as fluids entering said effluent receptacle;

returning said blood from said dialyzer at an outlet on said one side of said dialyzer to the patient under treatment;

sensing the pressure of said blood leaving said dialyzer;

routing a volume of dialysate substantially equivalent to the volume of ultrafiltrate leaving said other side of said dialyzer to a flow measurement pressure control unit;

measuring the volume of ultrafiltrate passing through said flow measurement pressure control unit in at least two fluid chambers of known volume that are alternately emptied and filled before passing the ultrafiltrate on to said effluent receptacle;

controlling fluid pressure in said flow measurement pressure control unit and in the hemodialysis system by controlling the amount of pressure that is placed upon the ultrafiltrate as it passes through said flow measurement pressure control unit;

comparing the pressure of blood exiting said dialyzer with the volume of ultrafiltrate passing through said flow measurement pressure control unit;

generating a signal proportional to the volume of ultrafiltrate leaving said flow measurement pressure control unit; and measuring the rate at which said ultrafiltrate leaves said flow measurement pressure control unit.

19. An automated method of hemodialysis treatment for controlling transmembrane pressure to a preset value, measuring said ultrafiltration rate, and measuring the total quantity of ultrafiltrate removed from a patient under treatment with a hemodialysis system, configurated in a recirculating dialysate system, comprising the steps of:

selecting an operating pressure across a semipermeable membrane in a dialyzer;

transporting blood from the patient into an inlet at one side of said dialyzer;

pumping dialysate from a source of fixed volume dialysate into an inlet at the other side of said dialyzer and then pumping said dialysate, including ultrafiltrate, out of said dialyzer at an outlet on said other side of said dialyzer back into said source of dialysate; the pumping rate for fluid entering said other side of said dialyzer being the same as fluids entering said source of dialysate;

returning said blood from said dialyzer at an outlet on said one side of said dialyzer to the patient under treatment;

sensing the pressure of said blood leaving said dialyzer;

routing a volume of dialysate substantially equivalent to the volume of ultrafiltrate leaving said other side of said dialyzer to a flow measurement pressure control unit;

measuring said volume of ultrafiltrate passing through said flow measurement pressure control unit in at least two fluid chambers of known volume that are alternately emptied and filled before passing the ultrafiltrate on to an effluent receptacle;

controlling fluid pressure in said flow measurement pressure control unit and in the hemodialysis system by controlling the amount of pressure that is placed upon the ultrafiltrate as it passes through said flow measurement pressure control unit;

comparing the pressure of blood exiting said dialyzer with the volume of ultrafiltrate passing through said flow measurement pressure control unit;

generating a signal proportional to the volume of ultrafiltrate leaving said flow measurement pressure control unit, and measuring the rate at which said ultrafiltrate leaves said flow measurement pressure control unit.

* * * * *